US010199130B2

(12) United States Patent
Olewine

(10) Patent No.: US 10,199,130 B2
(45) Date of Patent: Feb. 5, 2019

(54) METHODS AND DEVICES FOR ISOLATING LEAD 203

(71) Applicant: Lantheus Medical Imaging, Inc., North Billerica, MA (US)

(72) Inventor: Keith R. Olewine, Temple, NH (US)

(73) Assignee: Lantheus Medical Imaging, Inc., North Billerica, MA (US)

( * ) Notice: Subject to any disclaimer, the term of this patent is extended or adjusted under 35 U.S.C. 154(b) by 95 days.

(21) Appl. No.: 15/304,082

(22) PCT Filed: Apr. 15, 2015

(86) PCT No.: PCT/US2015/026015
§ 371 (c)(1),
(2) Date: Oct. 14, 2016

(87) PCT Pub. No.: WO2015/160981
PCT Pub. Date: Oct. 22, 2015

(65) Prior Publication Data
US 2017/0040074 A1 Feb. 9, 2017

Related U.S. Application Data

(60) Provisional application No. 61/979,957, filed on Apr. 15, 2014.

(51) Int. Cl.
*C22B 13/02* (2006.01)
*G21F 9/00* (2006.01)
*G21G 1/00* (2006.01)
*A61K 51/00* (2006.01)
*B01D 15/42* (2006.01)
*C22B 3/00* (2006.01)

(52) U.S. Cl.
CPC .............. *G21F 9/007* (2013.01); *A61K 51/00* (2013.01); *B01D 15/426* (2013.01); *C22B 13/04* (2013.01); *G21G 1/001* (2013.01); *G21G 2001/0094* (2013.01)

(58) Field of Classification Search
CPC ........... A61K 51/00; G21G 1/00; C22B 13/00
See application file for complete search history.

(56) References Cited

U.S. PATENT DOCUMENTS 4,011,307 A  3/1977 Lambrecht et al.

FOREIGN PATENT DOCUMENTS

WO   WO 98/08481 A2   3/1998
WO   WO 2013/174949 A1   11/2013

OTHER PUBLICATIONS

Paul P. Coetzee et al., Separation of 203 by ion-exchange chromatography on chelex 100 . . . , Talanta, vol. 36(4), 451-455. (Year: 1989).*
International Search Report and Written Opinion for PCT/US2015/026015 dated Aug. 21, 2015.
International Preliminary Report on Patentability for PCT/US2015/026015 dated Oct. 27, 2016.
Extended European Search Report for EP 15779451.2 dated Dec. 14, 2017.
[No Author Listed], Empore Extraction Disks General Guidelines for Applications. 3M. St. Paul, MN. Feb. 1996 4 pages.
Garmestani et al., Purification of cyclotron-produced 203Pb for labeling Herceptin. Nucl Med Biol. Apr. 2005;32(3):301-5.
Ion et al., Optimization of Preconcentration of Cadmium and Lead form Samples with Phosphate Matrices Using Chelex 100. Revue Roumaine de Chimie. 2006;51(12):1199-205.
Kadirvelu et al., Removal of heavy metals from industrial wastewaters by adsorption onto activated carbon prepared from an agricultural solid waste. Bioresour Technol. Jan. 2001;76(1):63-5.
Tandy et al., Extraction of heavy metals from soils using biodegradable chelating agents. Environ Sci Technol. Feb. 1, 2004;38(3):937-44.
Van Der Walt et al., Separation of (203)Pb by ion-exchange chromatography on chelex 100 after production of (203)Pb by the Pb(p, xn)(203)Bi→ EC.beta+ (203)Pb nuclear reaction. Talanta. Apr. 1989;36(4):451-5.

* cited by examiner

*Primary Examiner* — Michael G. Hartley
*Assistant Examiner* — Jagadishwar R Samala
(74) *Attorney, Agent, or Firm* — Wolf, Greenfield & Sacks, P.C.

(57) ABSTRACT

Methods for isolating Pb and/or Pb isotopes from various sources are provided. Compositions comprising Pb and/or Pb isotopes free of certain amounts of various contaminants are also provided.

4 Claims, 1 Drawing Sheet

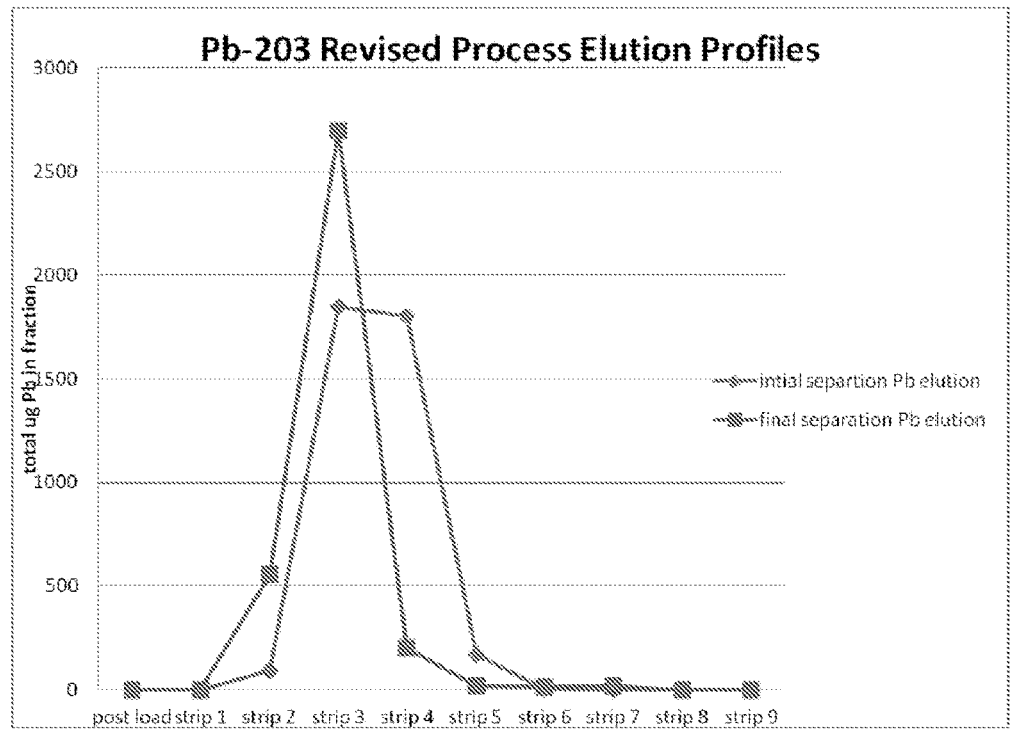

METHODS AND DEVICES FOR ISOLATING LEAD 203

RELATED APPLICATIONS

This application is a national stage filing under 35 U.S.C. § 371 of International Application No. PCT/US2015/026015, filed on Apr. 15, 2015, which was published under PCT Article 21(2) in English, and which claims the benefit of U.S. Provisional Application No. 61/979,957 filed on Apr. 15, 2014, the entire contents of each of which are incorporated by reference herein.

BACKGROUND OF INVENTION

Radioactive isotopes of many metallic elements have potential uses in the diagnosis and treatment of disease. The lead-203 isotope ($^{203}$Pb), for example, which has a half-life of about 52 hours and decays by electron capture, has excellent promise in medical diagnostics. As a result, recent advances in radioimmunotherapy and peptide targeted radiotherapy have created a great demand for $^{203}$Pb.

SUMMARY OF INVENTION $^{203}$Pb is an important isotope in certain medical applications. For example, because of its relatively short half-life (~52 hours) and decay scheme (279 KeV gamma energy, no beta emissions), $^{203}$Pb is particularly suited for imaging based diagnostics and radioimmunotherapeutic applications. With such medical applications, it is important to have a $^{203}$Pb source free of undesirable contaminants. However, $^{203}$Pb is typically generated as a byproduct of $^{201}$Pb and thallium-201 ($^{201}$Tl) production by cyclotrons. As a result, it must be isolated from the cyclotron waste stream, which contains metal contaminants, such as copper, nickel, iron, and zinc. The invention provides efficient means for doing so, based on the surprising discovery that under particular conditions $^{203}$Pb can be eluted almost exclusively from the cyclotron waste stream. As a result, other metal contaminants are left behind, thereby rendering the $^{203}$Pb in a suitable form for its further use in medical and other applications.

In one aspect, the invention provides a method comprising contacting a chelating resin that comprises iminodiacetic acid with a solution comprising Pb, and eluting Pb bound to the chelating resin with a heated sodium hydroxide solution, wherein the heated sodium hydroxide solution is at a temperature suitable for the selective elution of Pb.

In some embodiments, the temperature of the heated sodium hydroxide solution is about 85-95° C.

In another aspect, the invention provides a method comprising contacting a chelating resin that comprises iminodiacetic acid with a solution comprising Pb, and eluting Pb bound to the chelating resin with heated sodium hydroxide solution, wherein the temperature of the sodium hydroxide is at about 90° C.

In another aspect, the invention provides a method comprising selectively eluting bound Pb from a chelating resin. In some embodiments, the chelating resin comprises iminodiacetic acid. In some embodiments, bound Pb is eluted using a sodium hydroxide solution at a temperature of about 85-95° C. In some embodiments, bound Pb is eluted using a sodium hydroxide solution at a temperature of about 85° C. or higher.

In another aspect, the invention provides a method comprising selectively eluting bound Pb from a chelating resin using a sodium hydroxide solution at a temperature of about 85-95° C. In some embodiments, the chelating resin comprises iminodiacetic acid.

In some embodiments, Pb is $^{203}$Pb. In some embodiments, Ni, Cu, Zn, Fe and/or Th may also be bound to the resin.

In another aspect, the invention provides a composition comprising $^{203}$Pb and less than 0.1 µg/mCi Ni and/or less than 0.1 µg/mCi Cu and/or less than 0.5 µg/mCi Zn and/or less than 0.25 µg/mCi Fe and/or less than 0.05 µg/mCi Tl. In some embodiments, the composition further comprises sodium hydroxide.

BRIEF DESCRIPTION OF DRAWINGS

FIG. 1 is a graph depicting the amounts of lead eluted from Chelex 100 resins using heated (about 80-90° C.) 0.5 M sodium hydroxide (initial separation Pb elution; diamonds) and 1 M nitric acid (final separation Pb elution; squares).

DETAILED DESCRIPTION OF INVENTION

Radioisotopes of lead (Pb) have promising uses as therapeutic and diagnostic radiopharmaceuticals. For example, $^{212}$Pb is a promising α-particle emitting source, and targeted α-particle therapy offers a number of advantages in cancer therapies because of the combination of short path length (50-80 µm) and high linear energy transfer (100 KeV µm$^{-1}$) of this emission. One challenge associated with performing pre-clinical experiments with $^{212}$Pb, aside from its high cost, is the execution of accurate biodistribution and targeting assays of a $^{212}$Pb-radiolabeled therapeutic. Thus, a viable alternative is to employ $^{203}$Pb as a surrogate nuclide in such experiments. $^{203}$Pb has a favorable half-life (52 hours) and decays with 80.1% emission of γ-rays at 279 keV that is compatible with single photon emission computerized tomography (SPECT). This makes the radionuclide ideally suited as a matched radionuclide tracer for $^{212}$Pb targeted radionuclide therapies. Thus $^{203}$Pb is useful for imaging, tissue distribution studies, dosimetry data acquisition, as well as chemical exchange studies.

One approach for generating radionuclides is through generator systems wherein a longer-lived parent radionuclide is used to continuously generate, by radioactive decay, a shorter-lived daughter radionuclide of interest. The desired daughter radionuclide can be selectively separated and thus obtained by chemical means, such as ion-exchange chromatography. For example, $^{212}$Pb\$^{212}$Bi (bismuth-212) and $^{213}$Bi (bismuth-213) are members of decay chains of the long-lived parents $^{232}$Th (thorium-232) and $^{233}$U (uranium-233), respectively, and can therefore be produced by generators.

Conversely, $^{203}$Pb can only be produced with charged particle bombardments of either mercury or thallium. For example, $^{203}$Pb is produced as a byproduct of the $^{203}$Tl(p, 3n)$^{201}$Pb—$^{201}$Tl reaction in a cyclotron. However, $^{203}$Pb as a cyclotron byproduct contains problematic amounts of metal contaminants, such as nickel, copper, iron, zinc, etc. It is thus not directly suited for pharmaceutical or medical applications where such contaminants are undesirable. Additionally, current methodologies for isolating $^{203}$Pb using chelating resins do not provide effective means for selectively and significantly reducing metal contaminants as the resins are also able to bind other metals with similar affinity. For example, Pb$^{+2}$ and Ni$^{+2}$ have nearly equal affinities for Chelex 100 resins in nitrate or chloride solutions, making the selective elution of either metal difficult.

Accordingly, aspects of the present disclosure are based on the surprising discovery that heated sodium hydroxide solutions are able to selectively elute Pb (e.g., $^{203}$Pb) over other metals, from chelating resins. The chelating resins may be iminodiacetic acid containing chelating resins such as a Chelex 100 resin. Using a "cold" (e.g., no radiation) Pb isolation or separation model, in which a mixture of lead (Pb), copper (Cu), and nickel (Ni) were passed through and bound in a column containing Chelex 100, it was discovered that heated sodium hydroxide (e.g., 0.5-1.0 M, at about 90° C.) was able to elute Pb while Cu and Ni remained bound. This was surprising because, as noted above, Ni and Pb have similar affinities for iminodiacetic acid containing chelating resins such Chelex 100, under certain conditions. Additionally, as described herein, subsequent experimentation demonstrated that heated sodium hydroxide solutions were similarly able to selectively elute "hot" (e.g., radioactive) Pb (e.g., $^{203}$Pb) from resins such as Chelex 100 columns. This finding therefore reveals an effective means for the specific isolation of $^{203}$Pb from other metals, such as those that may be typically found, for example, in byproduct waste streams of $^{203}$Tl(p,3n)$^{201}$Pb—$^{201}$Tl cyclotron reactions.

Thus, some aspects of the invention provide methods for isolating lead (Pb) from Pb-containing solutions. In some embodiments, the Pb-containing solution comprises a Pb isotope, for example $^{200}$Pb, $^{201}$Pb, $^{202}$Pb, $^{203}$Pb, $^{204}$Pb, $^{205}$Pb, $^{206}$Pb, $^{207}$Pb, $^{208}$Pb, $^{209}$Pb, $^{210}$Pb, $^{211}$Pb, $^{212}$Pb, $^{213}$Pb and/or $^{214}$Pb. In some embodiments, the Pb-containing solution comprises $^{203}$Pb. In some embodiments, the solution comprises Pb or Pb isotopes and may further comprise one or more other metals, for example those typically found in a waste stream of a cyclotron reaction (e.g., thallium (Tl), Ni, Cu, iron (Fe), zinc (Zn)). It should be understood that Pb or Pb isotopes can be isolated from any solution containing additional constituents, from which it is desirable to separate Pb or Pb isotopes therefrom, according to the methods provided herein. By "solution" it is meant a liquid composition of two or more substances mixed together and uniformly dispersed, most commonly the result of dissolving a solid, fluid, or gas in a liquid. For example, Pb (and/or Pb isotopes) and additional compounds or metals may be dissolved in a liquid and such a liquid is a solution.

In some aspects, the method for isolating Pb and/or Pb isotopes involves the use of chelating resins, for example ion-exchange resins. In some embodiments, the chelating resin comprises iminodiacetic acid. Iminodiacetic acid, $HN(CH_2CO_2H)_2$, or "IDA," is a dicarboxylic acid amine. The iminodiacetate anion can act as a tridentate ligand to form a metal complex with two fused five membered chelate rings. The proton on the nitrogen atom can be replaced by a carbon atom of a polymer, such as styrene-divinylbenzene, to create a chelating resin (e.g., an ion-exchange resin). An example of such a resin is Chelex 100. In some embodiments, any chelating reagent or resin comprising IDA may be used according the methods provided herein. In some embodiments, the chelating resin is any form of Chelex 100. Chelex 100 resins are commercially available (from Bio-Rad, Hercules, Calif.).

In some embodiments, the method for isolating Pb and/or Pb isotopes involves eluting Pb and/or Pb isotopes bound to an ion-exchange resin including resins comprising IDA using a solution comprising sodium hydroxide. The solution is passed through the resin, thereby eluting the bound Pb and/or Pb isotopes.

In some embodiments, the solution is at least 0.01 molar (M), at least 0.05 M, at least 0.10 M, at least 0.15 M, at least 0.20 M, at least 0.25 M, at least 0.30 M, at least 0.35 M, at least 0.40 M, at least 0.45 M, at least 0.50 M, at least 0.55 M, at least 0.60 M, at least 0.65 M, at least 0.70 M, at least 0.75 M, at least 0.80 M, at least 0.85 M, at least 0.90 M, at least 0.95 M, at least 1.00 M, at least 1.05 M, at least 1.10 M, at least 1.15 M, at least 1.20 M, at least 1.25 M, at least 1.50 M, at least 1.75 M, at least 2.00 M, at least 2.25 M, at least 2.50 M, at least 3.00 M, at least 3.50 M, at least 4.00 M, at least 4.5 M, or at least 5.00 M sodium hydroxide.

In some embodiments, the sodium hydroxide solution used to elute the Pb and/or Pb isotopes is heated. In some embodiments, the sodium hydroxide solution is heated by first bringing the solution to a boil, and then allowing it to cool to about 90° C. before it is contacted with resin comprising bound Pb and/or Pb isotopes.

In some embodiments, the temperature of the sodium hydroxide solution is at a temperature suitable for the selective elution of Pb. For example, a temperature suitable for the selective elution of Pb means a temperature of about 99° C., of about 98° C., of about 97° C., of about 96° C., of about 95° C., of about 94° C., of about 93° C., of about 92° C., of about 91° C., of about 90° C., of about 89° C., of about 88° C., of about 87° C., of about 86° C., of about 85° C., of about 84° C., of about 83° C., of about 82° C., of about 81° C., or of about 80° C. In some embodiments, a temperature suitable for the selective elution of Pb means any temperature between about 80-100° C., 85-95° C., 96-94° C., 87-93° C., 88-92° C., or between about 89-91° C. In some embodiments, a temperature suitable for the selective elution of Pb means any temperature between about 80-90° C. a temperature suitable for the selective elution of Pb means any temperature between about 75-95° C.

In some embodiments, "selective elution" means that no more than about 1, 2, 3, 4, 5, 10, 15, 20, 25, 30, 35, 40, 45, 50, 60, 70, 80, 90, 100, 125, 150, 175, 200, 250, 300, 400, 500, 750, or 1000 parts per million (ppm) of an additional metal (e.g., Ni, Cu, Zn, Fe, Tl, etc.) elutes with the Pb. Methods for determining the amounts of metals (e.g., metal contaminants in a Pb elution) in a composition are known in the art, and include for example, inductively coupled plasma optical emission spectroscopy (ICP-OES) (e.g., for detecting trace metals) and high-purity germanium detector (HPGe) analysis (e.g., for detecting radioactive contaminants).

In some embodiments, selective elution means, e.g., with respect to eluting a Pb isotope (e.g., $^{203}$Pb), that less than about 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.25, 0.30, 0.35, 0.40, 0.45, or 0.50 µg Ni is eluted per mCi Pb isotope eluted.

In some embodiments, selective elution means that less than about 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.25, 0.30, 0.35, 0.40, 0.45, or 0.50 µg Cu is eluted per mCi Pb isotope eluted. The Pb isotope may be $^{203}$Pb.

In some embodiments, selective elution means that less than about 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.25, 0.30, 0.35, 0.40, 0.45, 0.50, 0.55, 0.60, 0.65, 0.70, 0.75, 0.80, 0.85, 0.90, 0.95, 1.00, 1.10, 1.20, 1.30, 1.40, or 1.50 µg Zn is eluted per mCi Pb isotope eluted. The Pb isotope may be $^{203}$Pb.

In some embodiments, selective elution means that less than about 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.25, 0.30, 0.35, 0.40, 0.45, 0.55, 0.60, 0.65, 0.70, 0.75, 0.80, 0.85, 0.90, 0.95, 1.00, 1.10, 1.20, 1.30, 1.40, or 1.50 µg Fe is eluted per mCi Pb isotope eluted. The Pb isotope may be $^{203}$Pb.

In some embodiments, selective elution means that less than about 0.005, 0.006, 0.007, 0.008, 0.009, 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.25, 0.30, 0.35, 0.40, 0.45, or 0.50 µg Tl is eluted per mCi Pb isotope eluted. The Pb isotope may be $^{203}$Pb.

According to another embodiment of the invention, compositions comprising Pb and/or Pb isotopes (e.g., $^{203}$Pb) are provided. In some embodiments, the composition is produced according to the methods provided herein, e.g., by eluting Pb and/or Pb isotopes from a chelating resin using heated sodium hydroxide.

In some embodiments, the composition comprises Pb isotopes (e.g., $^{203}$Pb).

In some embodiments, the composition comprises less than about 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.25, 0.30, 0.35, 0.40, 0.45, or 0.50 µg Ni per mCi Pb isotope. The Pb isotope may be $^{203}$Pb.

In some embodiments, the composition comprises less than about 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.25, 0.30, 0.35, 0.40, 0.45, or 0.50 µg Cu per mCi Pb isotope. The Pb isotope may be $^{203}$Pb.

In some embodiments, the composition comprises less than about 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.25, 0.30, 0.35, 0.40, 0.45, 0.50, 0.55, 0.60, 0.65, 0.70, 0.75, 0.80, 0.85, 0.90, 0.95, 1.00, 1.10, 1.20, 1.30, 1.40, or 1.50 µg Zn per mCi Pb isotope. The Pb isotope may be $^{203}$Pb.

In some embodiments, the composition comprises less than about 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.25, 0.30, 0.35, 0.40, 0.45, 0.55, 0.60, 0.65, 0.70, 0.75, 0.80, 0.85, 0.90, 0.95, 1.00, 1.10, 1.20, 1.30, 1.40, or 1.50 µg Fe per mCi Pb isotope. The Pb isotope may be $^{203}$Pb.

In some embodiments, the composition comprises less than about 0.005, 0.006, 0.007, 0.008, 0.009, 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.25, 0.30, 0.35, 0.40, 0.45, or 0.50 µg Tl per mCi Pb isotope. The Pb isotope may be $^{203}$Pb.

EXAMPLES

The present invention will be more specifically illustrated by the following Examples. However, it should be understood that the present invention is not limited by these Examples in any manner.

Example 1: Natural Lead is Selectively Eluted from Chelex 100 Resin Using Heated Sodium Hydroxide In order to determine whether lead (Pb) could be selectively eluted using heated sodium hydroxide in the absence of radiation (e.g., from $^{203}$Pb), a cold process was performed using approximately 5 mg each of copper (Cu), nickel (Ni) and Pb ICP standards. The standards were pooled together and diluted to simulate a target solution without thallium (Tl).

A Chelex 100 column (Bio-Rad), ammonium form, 14 ml resin bed, was conditioned with 25 ml of 1 M ammonium nitrate.

The simulated target solution was pH adjusted using concentrated ammonium hydroxide and 1 M nitric acid to a final value between pH 5-6. The adjusted solution was loaded onto the conditioned Chelex 100 ammonium form column. Approximately 75 ml of 0.5 M sodium hydroxide was heated to boiling on a hotplate. The sodium hydroxide was added to the column in 10-20 ml increments to strip or remove the natural lead from the column. The temperature of the sodium hydroxide was measured to be between 80-90° C. for each of the strip portions. Mild air pressure (~0.5 PSI) was applied to the column during the strip due to backpressure. Cu and Ni remained on the column by visual examination.

The resulting natural lead solution was passed through one additional Chelex column in the same manner. The lead was removed from the second column using 1 M Nitric acid in 10-20 ml increments.

Each of the fractions from load through strip was reserved individually for inductively coupled plasma (ICP) analysis. FIG. 1 displays the elution profile for the lead on each of the Chelex columns. Notably, two 10-20 ml increments (strips) of heated (e.g., between about 80-90° C.) 0.5 M sodium hydroxide was effective in eluting the bound Pb, while Cu and Ni remained bound (FIG. 1, and data not shown).

Example 2: $^{203}$Pb is Selectively Eluted from Chelex 100 Resin Using Heated Sodium Hydroxide Six $^{203}$Pb elution processes were performed using cyclotron irradiated natural thallium targets in series of three targets, each by methods described above with minor modifications.

The first three runs were performed using a two column system. Mild air pressure (0-2 PSI) was used inside the process cell to increase column speed and aid in stripping of $^{203}$Pb from the column. Loading of the column during the initial separation of the Tl from the Pb isotopes was performed with no air pressure added to the column (gravity fed).

$^{203}$Pb was removed from the columns using hot (~90° C.) 0.5 M sodium hydroxide. The $^{203}$Pb was removed from the second column with 1 M nitric acid. The nitric acid fraction was taken to dryness and stocked in 0.5 M hydrochloric acid. Evidence of significant solids (salts) was observed upon the solution reaching dryness.

The stock solution was assayed via dilution on a dose calibrator. Radionuclidic purity samples (HPGe analysis) were prepared via serial dilution from the stock solution. ICP samples were prepared at 1 mCi/ml at calibration for analysis. Table 2 contains the ICP data for the Series 1 targets.

The second series of targets was performed using a three column system.

The third column was added in an attempt to reduce metallic contaminants observed in the series 1 targets. The third column also incorporated a purified water rinse of the column prior to stripping of the $^{203}$Pb in order to minimize the salts observed at beaker dryness.

An additional change to the series 2 targets was the stocking of the lot in 0.5 M nitric acid. Table 4 compares the values for the Series 1 (2 column) vs. the Series 2 (3 column) systems.

Column performance post $^{203}$Pb separation was analyzed on the sixth process. The analysis was performed by removing all metal from the columns using 1 molar nitric acid. The resulting solutions were analyzed by ICP for metals and HPGe for radionuclidic concentration. Table 1 contains the values for the ICP analysis in total micrograms removed from the column.

Example 3: Isolation of $^{203}$Pb

Purpose: The following describes an exemplary protocol for isolating $^{203}$Pb from natural thallium targets and other metals present, for example, from Tl(p,3n)$^{201}$Pb—$^{201}$Tl cyclotron reactions.

Materials and equipment: Glass wool, glass beakers (various sizes, as needed), column stand, hotplate/stirrer, poly bottles (various sizes, as needed), pipets (various sizes as needed), 10 cc vials with septa as needed, 1 dram screw top vials as needed, 20 ml LSC vials as needed, analytical balance, pH meter, Capintec ionization chamber, ½ inch pig, process cell, etching vessel.

Reagents: 1 N ammonium nitrate, 1.0 M sodium hydroxide, 0.5 M hydrochloric acid (0.5M HCl), 0.5 M nitric acid (0.5M HNO3), Bio-Rad Chelex 100 column (ammonium form), pH 4 Buffer, pH 7 Buffer, ICP grade water, 1 M Nitric Acid.

Initial separation of $^{203}$Pb from a natural thallium target.

0-2 PSI of air pressure can be applied to the columns as each step is performed. Loading of the activity should be performed with less than 0.5 PSI of air applied.

1) Condition a Chelex 100 column with 25 ml of ammonium nitrate (column 1).
2) Prepare a glass wool column.
3) Calibrate the pH meter.
4) Place the glass wool column and etching vessel into a process cell.
5) Carefully remove the etching vessel and insert a new etching jig into the apparatus.
6) Place the conditioned Chelex column, beakers and reagents into the process cell.
7) Obtain the irradiated natural thallium target, and estimate the activity on the target: Activity range=0.5 mCi/uAmp hr×uAmp hr to 1.5 mCi/uAmp hr×uAmp hr.
8) Heat approximately 110-120 ml of nitric acid to boiling on the hotplate. Once boiling pour approximately 90 ml into the etching jig.
9) Etch the target in hot 1 M nitric acid until the thallium is completely dissolved.
10) Pass the etch solution through the glass wool column to remove particulates.
11) Rinse the target and glass wool column with approx. 20 ml of hot nitric acid.
12) Discard the glass wool column.
13) pH adjust the etch solution to 5-6 using concentrated ammonium hydroxide. Back titrate with 1 M nitric acid as needed.
14) Load the pH adjusted solution onto the Chelex column.
15) Wash the Chelex column with 150-175 ml of 1 M ammonium nitrate.
16) Place a 150 ml beaker on the hotplate and heat 100 ml of 1 M sodium hydroxide to a boil. Turn off the hotplate once the sodium hydroxide is at a boil.
17) Strip the $^{203}$Pb from the column using the heated sodium hydroxide (at a temperature of about 90° C.) in 10-20 ml increments until the $^{203}$Pb is removed from the column.
18) Discard the column.
19) Obtain a reading of the $^{203}$Pb strip solution. Verify complete removal by measuring the column on the in-cell ion chamber.

$^{203}$Pb Final Purification.

1) Condition a second Chelex column with 25 ml of ammonium nitrate and place the conditioned column into the process cell (column 2).
2) pH adjust the $^{203}$Pb strip solution to 5-6 using concentrated ammonium hydroxide. Back titrate with 1 M nitric acid as needed.
3) Load the pH adjusted solution onto the Chelex column.
4) Wash the chelex column with 150-175 ml of 1 M ammonium nitrate.
5) Place a 150 ml beaker on the hotplate and heat 100 ml of 1 M sodium hydroxide to a boil. Turn off the hotplate once the sodium hydroxide is at a boil.
6) Strip the $^{203}$Pb from the column using the heated sodium hydroxide in 10-20 ml increments until the $^{203}$Pb is removed from the column.
7) Condition a third Chelex column with 25 ml of ammonium nitrate and place the conditioned column into the process cell.
8) pH adjust the second $^{203}$Pb strip solution to 5-6 using concentrated ammonium hydroxide. Back titrate with 1 M nitric acid as needed.
9) Load the pH adjusted solution onto the Chelex column.
10) Wash the Chelex column with 150-175 ml of 1 M ammonium nitrate.
11) Once the ammonium nitrate elutions are completed, wash the column with 60 of purified water.
12) Strip the column with 1 M nitric acid in 10-20 ml increments until the $^{203}$Pb is removed from the column.

Stocking Isolated $^{203}$Pb.

1) Evaporate the collected $^{203}$Pb solution in a 250 mL glass beaker to dryness on the hot plate. Record condition below.
2) Obtain a tare weight of a 10 cc septa "S" vial, and record.
3) Place the S vial into a 0.22 μm filter stand and remove the septum.
4) Place a 30 cc syringe with conditioned filter into the stand and S vial. Remove the plunger.
5) Add 2-3 mL 0.5 N HNO$_3$ to the $^{203}$Pb in the beaker using a clean 5 mL plastic pipet. Heat on the hot plate until steaming begins and transfer to the syringe. Push the volume transferred through the filter into the S vial.
6) Repeat step 5) two to four times until the $^{203}$Pb is stocked in approximately 10 ml.

Assaying for $^{203}$Pb Activity.

1) Obtain a gross of weight of the S vial after completion of stocking the isolated $^{203}$Pb, and obtain a net weight after subtracting the tare weight of the empty S vial.
2) Obtain a tare weight of an additional S vial, denoted "S1."
3) Mix the contents of the S vial thoroughly using a 1 ml pipet. Remove approximately 0.5 mL from the "S" vial using a 1 mL pipet and transfer to the "S1" vial. Obtain a gross weight, and then a net weight by subtracting the S1 tare weight.
4) Place the S1 vial into a ½ inch pig.
5) Crimp the S1 vial and transfer to the Capintec ionization chamber station.
6) Set the ionization chamber "activity range" dial to auto range. Set the potentiometer setting of the Capintec to 344 which is the recommended setting for $^{203}$Pb. Record the background below. Transfer the S1 vial to the Capintec holder using tongs and lower it all the way into the chamber. Record gross activity and subtract the background to obtain net mCi.

7) Calculate the S vial concentration (mCi/g) using the above determined activity, and the net weights of S and S1 vials.

TABLE 1

Post $^{203}$Pb separation analysis of metals on Chelex 100. All values in micrograms (μg)

|  | Tl* | Pb | Ni | Fe | Zn | Cu |
|---|---|---|---|---|---|---|
|  | All values in micrograms (μg) | | | | | |
| column 1 | 236.3 | 59.7 | 7215.5 | 12.0 | 57.6 | 980.4 |
| column 2 | 0.0 | 2.1 | 10.5 | 0.8 | 5.9 | 24.3 |
| column 3 | 0.4 | 1.0 | 0.5 | 4.3 | 6.9 | 0.3 |
| Sum C1-C3 | 236.6 | 62.7 | 7226.4 | 17.0 | 70.4 | 1005.0 |

*Initial thallium mass on target 2.5-9.0 grams.

TABLE 2

Series 1 Targets.

Total μg metals in solution

| Element | Run 1 | Run 2 | Run 3 | Average |
|---|---|---|---|---|
| Pb | 107 | 51 | 15.51 | 57.84 |
| Fe | 41.11 | 86.89 | 16.65 | 48.22 |
| Tl | 13.5 | 4.74 | 8.9 | 9.05 |
| Cu | 3.22 | 3.16 | 2.51 | 2.96 |
| Ni | 2.22 | 3.16 | 2.28 | 2.55 |
| Zn | NA | NA | NA | NA |

TABLE 3

Series 2 Targets.

Total μg metals in solution

| Element | Run 4 | Run 5 | Run 6 | Average |
|---|---|---|---|---|
| Pb | 26.38 | 13.78 | 38.58 | 26.25 |
| Fe | 4.32 | 6.17 | 6.49 | 5.66 |
| Tl | 0.15 | 0.14 | 0.05 | 0.11 |
| Cu | 4.21 | 0.87 | 0.72 | 1.93 |
| Ni | 0.68 | 0.26 | 0.39 | 0.44 |
| Zn | 30.39 | 6.98 | 3.18 | 13.52 |

TABLE 4 difference in elemental contaminants between two and three column system.

| Element | Average Series 1 | Average Series 2 | % Difference * |
|---|---|---|---|
| Pb | 57.84 | 26.25 | −54.6 |
| Fe | 48.22 | 5.66 | −88.3 |
| Tl | 9.05 | 0.11 | −98.7 |
| Cu | 2.96 | 1.93 | −34.8 |
| Ni | 2.55 | 0.44 | −82.6 |
| Zn | NA | 13.52 | −54.6 |

* The percent difference = (Ave. Series 2 − Ave. Series 1)/Ave. Series 1 * 100

EQUIVALENTS AND SCOPE

Those skilled in the art will recognize or be able to ascertain using no more than routine experimentation many equivalents to the specific embodiments described herein. The scope of the present invention is not intended to be limited to the above Description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It should it be understood that, in general, where the invention, or aspects of the invention, is/are referred to as comprising particular elements, features, etc., certain aspects of the invention or embodiments of the invention consist, or consist essentially of, such elements, features, etc. For purposes of simplicity those embodiments have not been specifically set forth in haec verba herein. It is also noted that the term "comprising" is intended to be open and permits the inclusion of additional elements or steps.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention can be excluded from any one or more claims, for any reason, whether or not related to the existence of prior art.

All references cited herein, including patents, published patent applications, and publications, are incorporated by reference in their entirety.

What is claimed is:

1. A method, comprising
   contacting a chelating resin that comprises iminodiacetic acid with a solution comprising Pb, and
   eluting the Pb bound to the chelating resin with a heated sodium hydroxide solution, wherein the heated sodium hydroxide solution is at a temperature suitable for the selective elution of Pb.

2. The method of claim 1, wherein the temperature of the heated sodium hydroxide solution is about 85-95° C.

3. A method, comprising
   contacting a chelating resin that comprises iminodiacetic acid with a solution comprising Pb, and
   eluting the Pb bound to the chelating resin with heated sodium hydroxide solution, wherein the temperature of the sodium hydroxide is at about 90° C.

4. A method, comprising
   eluting Pb from a chelating resin using a sodium hydroxide solution at a temperature of about 85-95° C. or of about 85° C. or higher.

* * * * *